United States Patent
Mullen

(10) Patent No.: US 9,986,970 B2
(45) Date of Patent: Jun. 5, 2018

(54) APPARATUS AND METHOD FOR AIDING EXTREMITY ULTRASONOGRAPHY

(71) Applicant: General Electric Company, Schenectady, NY (US)

(72) Inventor: Paul Mullen, Waukesha, WI (US)

(73) Assignee: General Electric Company, Schenectady, NY (US)

( * ) Notice: Subject to any disclaimer, the term of this patent is extended or adjusted under 35 U.S.C. 154(b) by 262 days.

(21) Appl. No.: 14/144,824

(22) Filed: Dec. 31, 2013

(65) Prior Publication Data

US 2015/0182189 A1      Jul. 2, 2015

(51) Int. Cl.
*A61B 8/00*      (2006.01)
*A61B 8/08*      (2006.01)

(52) U.S. Cl.
CPC ............. *A61B 8/4227* (2013.01); *A61B 8/08* (2013.01); *A61B 8/4281* (2013.01); *A61B 8/40* (2013.01); *A61B 8/4444* (2013.01)

(58) Field of Classification Search
CPC combination set(s) only.
See application file for complete search history.

(56) References Cited

U.S. PATENT DOCUMENTS

| | | | | |
|---|---|---|---|---|
| 1,617,942 | A * | 2/1927 | Foulke | A61F 5/05875 602/22 |
| 3,710,779 | A * | 1/1973 | Bunnell | A61K 47/10 523/105 |
| 4,143,653 | A * | 3/1979 | Wichman | A61F 5/05875 602/22 |
| 5,598,846 | A * | 2/1997 | Peszynski | A61B 5/6826 600/444 |
| 2008/0300488 | A1* | 12/2008 | Schutz | A61B 5/6826 600/459 |
| 2011/0263982 | A1* | 10/2011 | Kano | A61B 8/06 600/443 |
| 2013/0158365 | A1 | 6/2013 | Chey et al. | |
| 2013/0237819 | A1* | 9/2013 | Sun | A61B 8/467 600/437 |
| 2013/0261460 | A1* | 10/2013 | Sakaguchi | A61B 8/4254 600/443 |
| 2014/0267116 | A1* | 9/2014 | Weiner | A61F 5/05866 345/173 |

FOREIGN PATENT DOCUMENTS

WO      WO 9712552 A1 *   4/1997   ........... A61B 8/0866

* cited by examiner

*Primary Examiner* — Serkan Akar
*Assistant Examiner* — Farshad Negarestan

(57) ABSTRACT

An apparatus for releasably coupling an ultrasound probe with an extremity comprises a housing adapted to substantially surround the extremity. The housing comprises a first opening adapted to receive the ultrasound probe and position the probe in contact with the extremity.

11 Claims, 5 Drawing Sheets

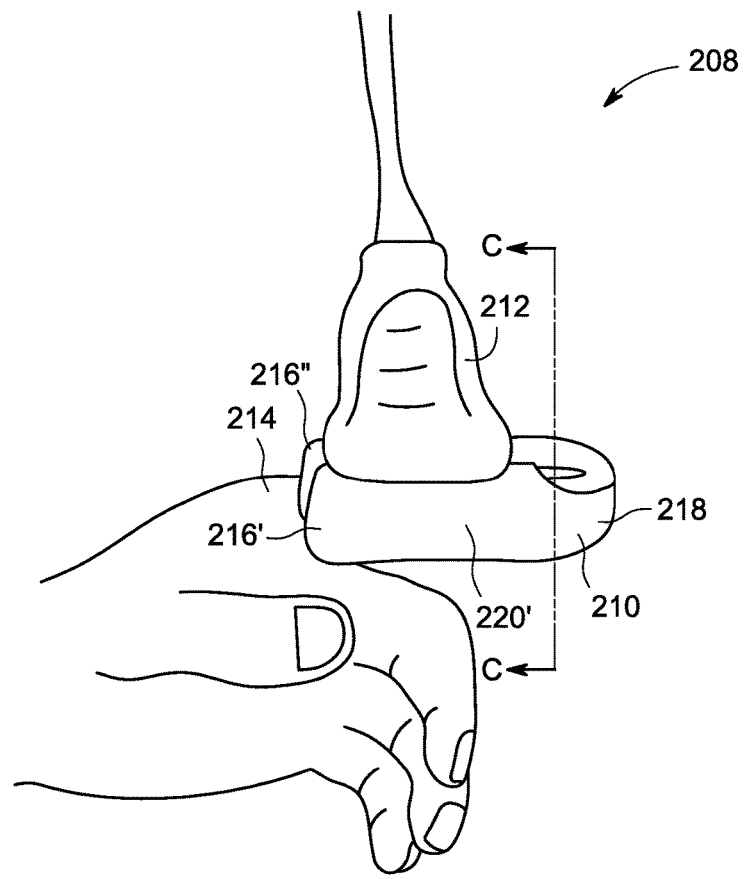
FIG. 7
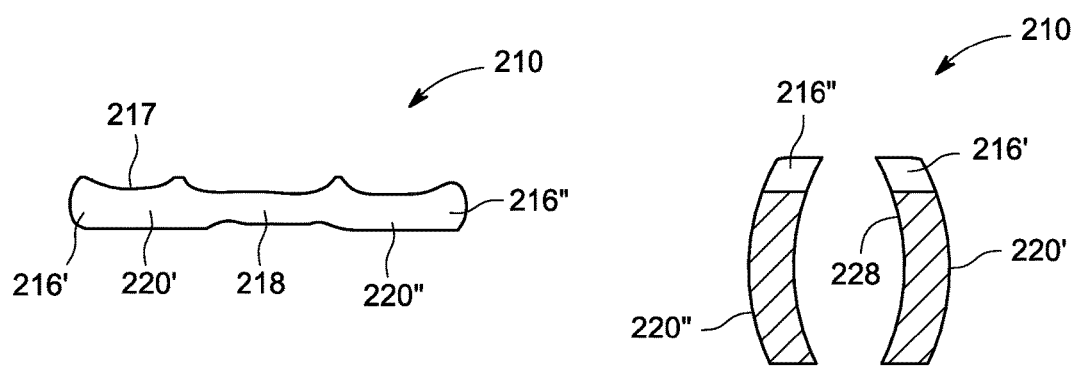
FIG. 8
FIG. 9

APPARATUS AND METHOD FOR AIDING EXTREMITY ULTRASONOGRAPHY

BACKGROUND OF THE INVENTION

The subject matter disclosed herein relates to ultrasonography of extremities, and more specifically an apparatus to aid in reducing operator variability.

A key problem in musculoskeletal ("MSK") ultrasonography is the variability of the operator in the placement of the transducer. Both the location of the transducer and the pressure applied by the operator can impact the quality of the exam. These factors may also vary amongst operators. Holding the transducer in contact with ultrasound gel on an extremity of a patient while applying the appropriate amount of pressure is a skill that can be acquired, but is difficult. In some studies of the extremities, too much pressure on the extremity (for example a finger) can temporarily cut off circulation, which may be important to the diagnosis. Generally, operators put gel on the extremity and then work to acquire the skill required to both maintain contact while maintaining the appropriate amount of pressure and to find the peak blood flow angle. This may result in increased exam times and workflow inefficiencies.

Therefore, an apparatus and method to standardize what is typically a fairly operator-dependent procedure, by reducing variability due to transducer placement and pressure, is desired. This could lead to significantly improved inter-operator variability in MSK studies. Additionally, this approach would make the above-mentioned objective of applying the appropriate amount of pressure during scanning less skill-dependent and thus increase exam quality for less experienced operators.

BRIEF DESCRIPTION OF THE INVENTION

The above-mentioned shortcomings, disadvantages and problems are addressed herein which will be understood by reading and understanding the following specification.

In an embodiment, an apparatus for releasably coupling an ultrasound probe with an extremity comprises a housing adapted to substantially surround the extremity. The housing comprises a first opening adapted to receive the ultrasound probe and position the probe in contact with the extremity.

In another embodiment, a system for reducing variability in ultrasound procedures of an extremity comprises a housing adapted to substantially surround the extremity and comprises a first mating element. The system further comprises an ultrasound probe comprising a second mating element, wherein the first mating element and the second mating element are adapted to mate.

In another embodiment, a method of performing an ultrasound scan on a patient extremity utilizing an ultrasound probe comprises applying ultrasonic gel to an interior of a housing and positioning the housing about the extremity. The method further comprises mating an ultrasound probe to the housing, wherein when mated a tip of the ultrasound probe is in contact with the ultrasonic gel.

Various other features, objects, and advantages of the invention will be made apparent to those skilled in the art from the accompanying drawings and detailed description thereof.

BRIEF DESCRIPTION OF THE DRAWINGS

FIG. 7 is a perspective view of a system in accordance with an embodiment;

FIG. 8 is a side elevation view of the housing shown in FIG. 7;

FIG. 9 is a cross-sectional view of the housing taken from the line C-C in FIG. 7;

DETAILED DESCRIPTION OF THE INVENTION

In the following detailed description, reference is made to the accompanying drawings that form a part hereof, and in which is shown by way of illustration specific embodiments that may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken as limiting the scope of the invention.

Figure 1:
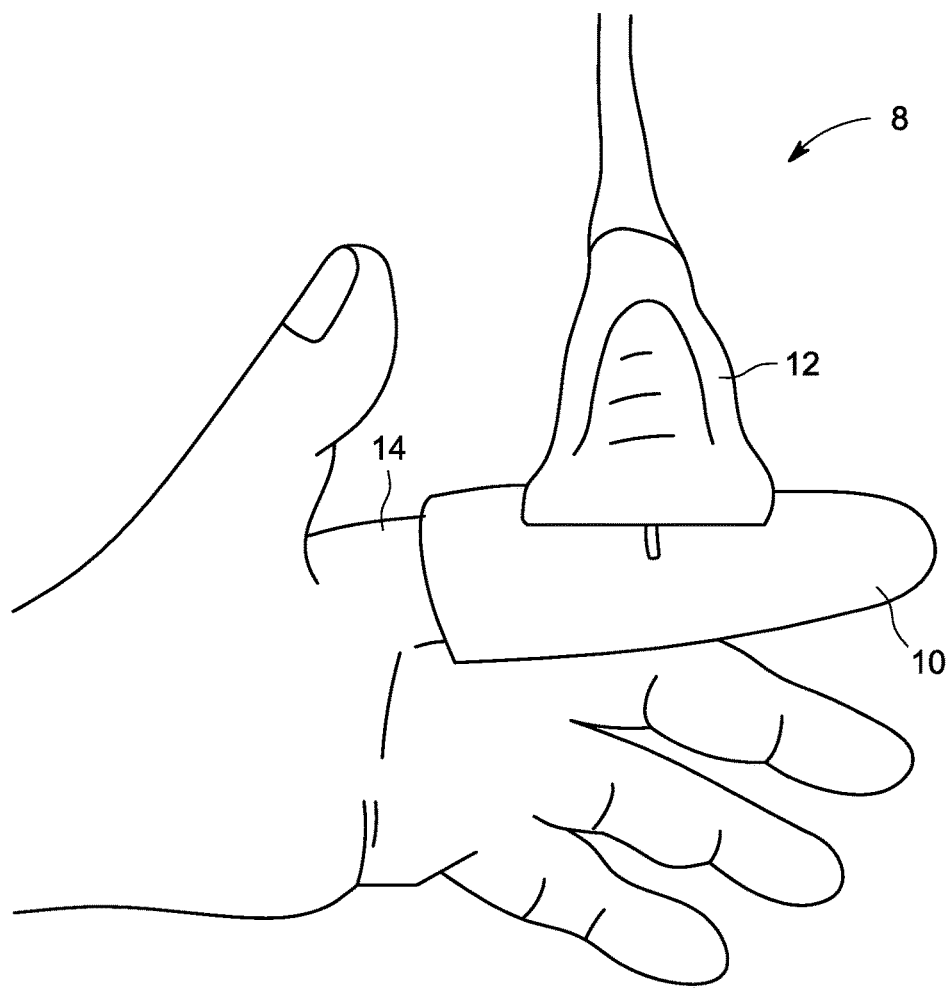
FIG. 1 is a perspective view of a system in accordance with an embodiment.

Referring to FIG. 1, a perspective view of a system 8 is shown in accordance with an embodiment. The system 8 comprises a housing 10 and an ultrasound probe 12. The housing 10 will hereinafter be described as a housing for use with releasably coupling a healthcare device, such as ultrasound probe 12, with an extremity 14, such as a finger. It should be appreciated, however, that other types of healthcare devices which are required to stay in contact or close proximity with the surface of a human or animal body may be envisioned for use with the housing 10. It should further be appreciated that other extremities 14 such as a hand, wrist, toe or foot may be mated by the housing 10 to the probe 12 or healthcare device.

Figure 2:
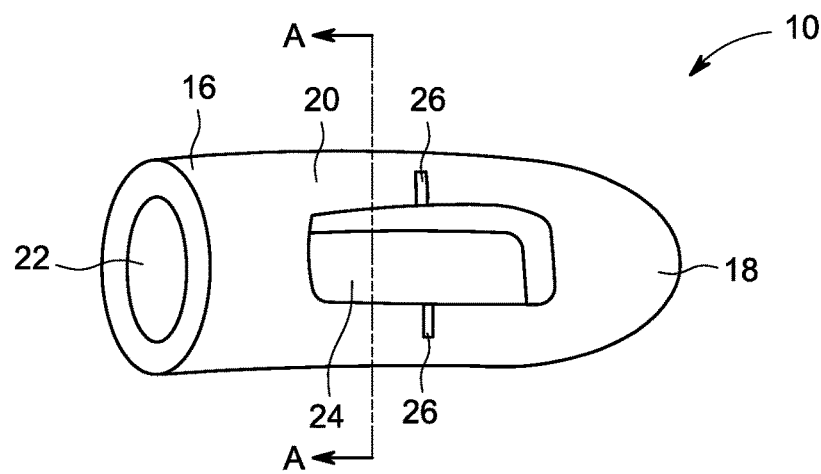
FIG. 2 is a perspective view of the housing shown in FIG. 1.
Figure 3:
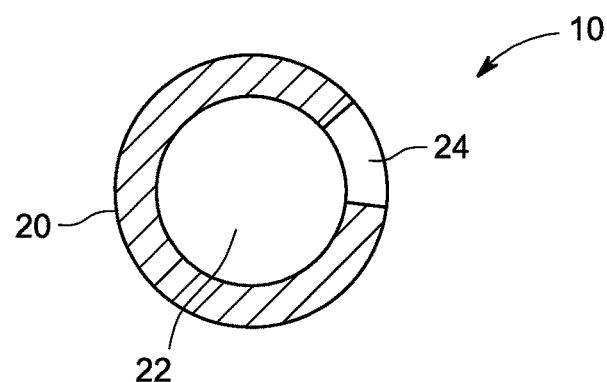
FIG. 3 is a cross-sectional view of the housing taken from the line A-A in FIG. 2.
Figure 4:
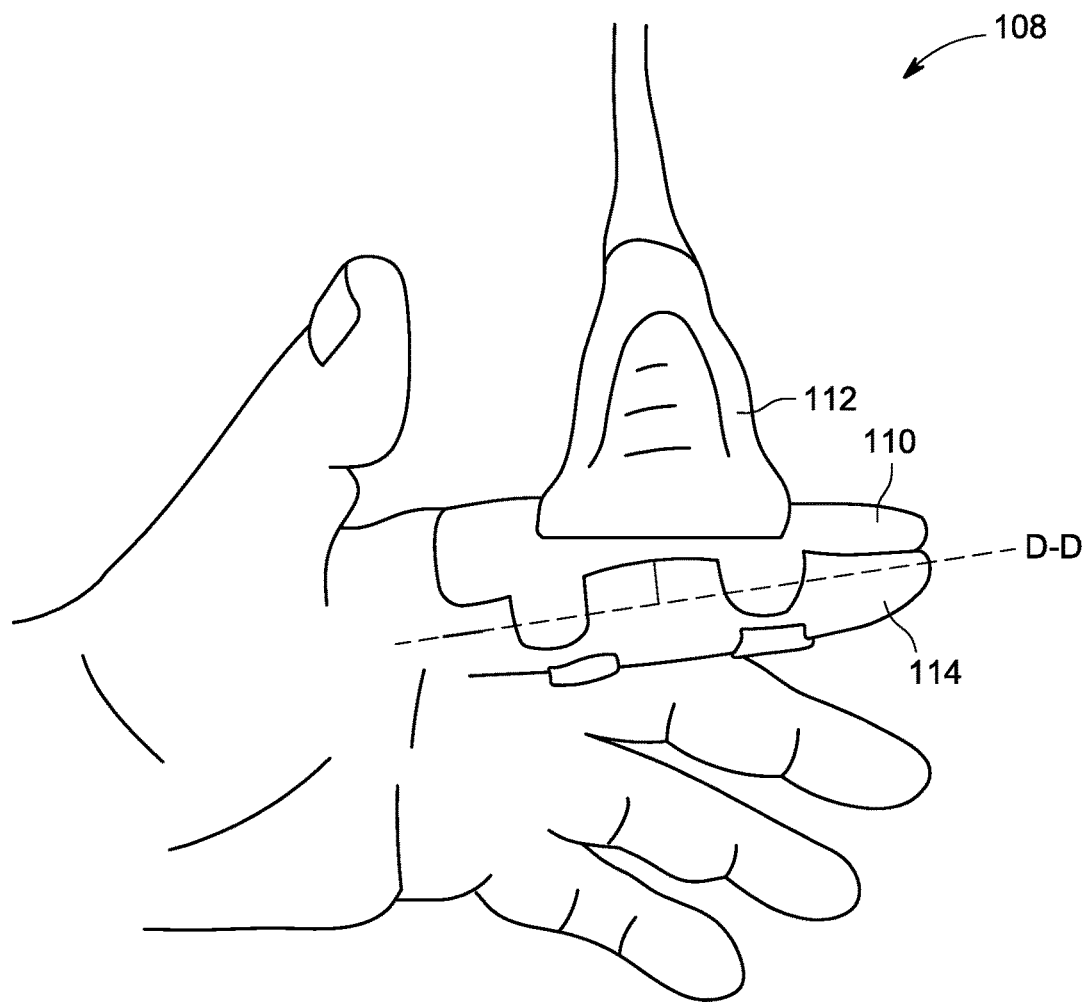
FIG. 4 is a perspective view of a system in accordance with an embodiment.

In accordance with an embodiment as shown in FIGS. 1-3, the housing 10 is adapted to substantially surround the extremity 14. In some embodiments, the housing 10 is comprised of a flexible material, such as a latex rubber, or a fabric. The flexible material may also be adhesive so as to stick to the extremity 14. In other embodiments, the housing 10 is comprised of a substantially rigid material that may generally immobilize the extremity 14. The housing 10 comprises a proximate end 16, a distal end 18, and a center portion 20 connecting the proximate end 16 to the distal end 18. The proximate end 16 comprises an opening 22 that is adapted to receive the extremity 14. The opening 22 may also be adapted to receive ultrasonic gel. The ultrasonic gel may be any medium known in the art to conduct ultrasound waves from probe 12 to the imaging target, such as the extremity 14. The distal end 18 may be closed as depicted in this embodiment. Alternately, the distal end 18 may be open, as depicted in FIG. 4 and described below, thereby permitting the extremity 14 to extend beyond distal end 18 of the housing 10.

The center portion 20 comprises an opening 24 that is adapted to releasably receive the ultrasound probe 12. When the ultrasound probe 12 is received by the housing 10 via opening 24, the probe 12 is positioned in contact, or mated, with extremity 14. The opening 24 may also be adapted to receive ultrasonic gel.

The center portion 20 may also comprise one or more position marking 26. The position marking 26 is intended to aid the clinician in position the housing 10 on the extremity 14. Various embodiments of the position marking 26 may be envisioned. For example, the position marking 26 may be printed on the surface of housing 10 or etched into the surface of housing 10. The center portion 20 may further comprise a plurality of position markings 26 that are configured to indicate ideal transducer placement to capture a series of standard clinical images. In another embodiment, the markings 26 may be positioned at the proximate end 16 and distal end 18 about the circumference of the housing 10 to indicate the angulation of the probe 12 along the axis of the extremity 14.

A cross-sectional view at the center portion 20 of housing 10, taken along the line A-A in FIG. 2, is shown in FIG. 3. At the center portion 20, the housing 10 has a generally circular cross-section, configured to substantially surround the extremity 14.

Referring to FIG. 4, a perspective view of a system 108 is shown in accordance with an embodiment. The system 108 comprises a housing 110 and an ultrasound probe 112. The housing 110 will hereinafter be described as housing for use with releasably coupling a healthcare device, such as ultrasound probe 112, with an extremity 114, such as a finger. It should be appreciated, however, that other types of healthcare devices which are required to stay in contact or close proximity with the surface of a human or animal body may be envisioned for use with the housing 110. It should further be appreciated that other extremities such as a hand, wrist, toe or foot may be mated by the housing 110 to the probe 112 or healthcare device.

Figure 5:
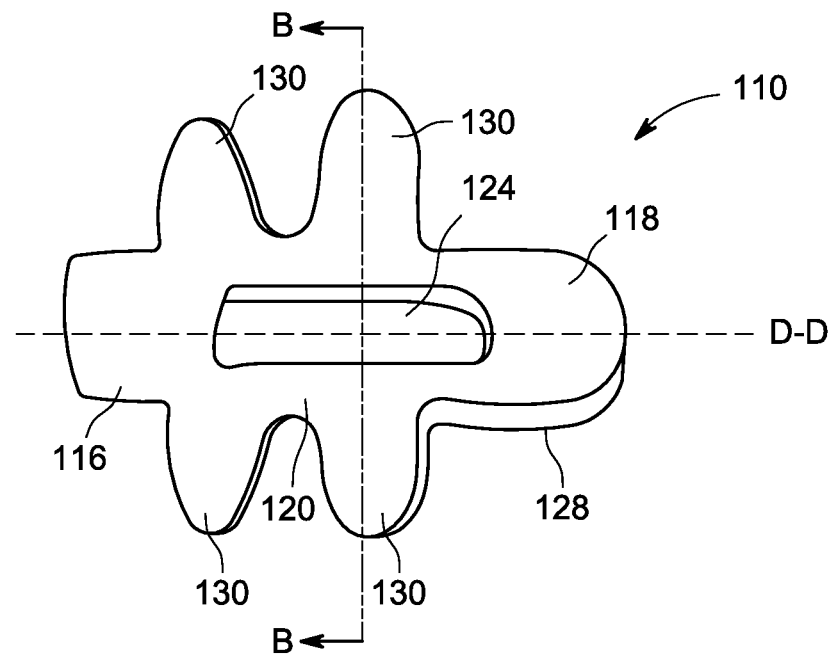
FIG. 5 is a perspective view of the housing shown in FIG. 4.
Figure 6:
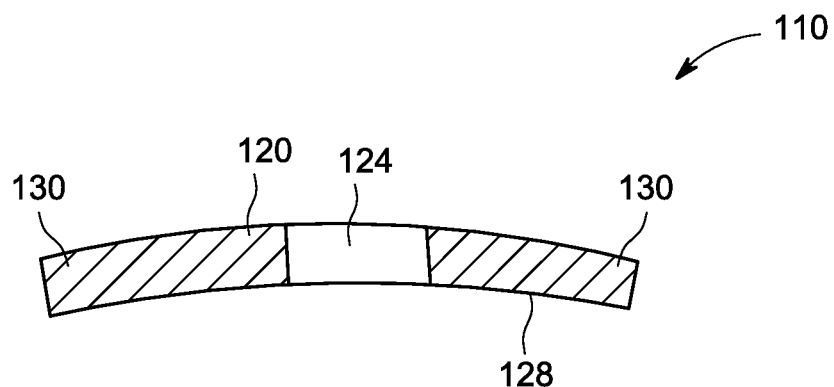
FIG. 6 is a cross-sectional view of the housing taken from the line B-B in FIG. 3.

In accordance with the embodiment, and as shown in FIGS. 4-6, the housing 110 comprises a proximate end 116, a distal end 118, and a center portion 120 connecting the proximate end 116 to the distal end 118. The housing 110, when not positioned to substantially surround the extremity 114, has a substantially planar configuration and is generally parallel to an axis D-D extending through the extremity 114, as illustrated in FIGS. 4-6. FIG. 6 shows a cross-sectional view of the housing 110 taken along the line B-B in FIG. 5. In some embodiments, the housing 110 is comprised of a flexible material, such as a latex rubber, or a fabric. The flexible material may also be adhesive so as to stick to the extremity 114. In other embodiments, the housing 110 is comprised of a substantially rigid material that may generally immobilize the extremity 114.

Housing 110 is adapted at one or more portions to substantially surround and potentially immobilize the extremity 114, such as at protrusions or tabs 130 (see FIG. 5). The distal end 118 may be open, thereby permitting the extremity 114 to extend beyond the distal end 118 of the housing 110. The center portion 120 comprises an opening 124 that is adapted to releasably receive the ultrasound probe 112. When the ultrasound probe 112 is received by housing 110 via opening 124, the probe 112 is positioned in proper contact with extremity 114.

The tabs 130 of the housing 110 are adapted to wrap about at least a portion of the extremity 114 to securely mate the housing 110 to the extremity 114. Each tab 130 is bendable or moldable. It should be appreciated that various embodiments of the tabs 130 may be envisioned. For example, in the embodiment depicted in FIGS. 3-6, the housing 110 comprises two pairs of tabs 130, each pair configured with one tab 130 on each lateral side of the housing 110 and the axis D-D. However, the housing 110 may have fewer or more tabs. It should further be appreciated that other configurations of tabs 130 may be envisioned. For example, in the embodiment depicted in FIGS. 3-6, the tabs 130 are located in the center portion 120. However, tabs 130 could be located closer to or at the proximate end 116 or nearer the distal end 118, or any combination thereof. Additionally, the shape or geometry of the tabs 130 may vary.

The housing 110 may be configured to surround various degrees of the circumference of extremity 114. For example, as depicted in FIG. 3, the portion of housing 10 with tabs 130 may surround approximate 315 degrees of the extremity. However, it should be appreciated that at least 180 degrees of the circumference of the extremity 114 should be surrounded by at least one portion of the housing 110 to ensure the housing 110 remains securely in place without need for adhesives.

Referring to FIG. 7, a perspective view of a system 208 is shown in accordance with an embodiment. The system 208 comprises a housing 210 and an ultrasound probe 212. As with the previously described embodiments, the housing 210 will hereinafter be described as a housing for use with releasably coupling or positioning a healthcare device, such as the ultrasound probe 212, in proper contact with an extremity 214, such as a finger, for an imaging procedure. It should be appreciated, however, that other types of healthcare devices which are required to stay in contact or close proximity with the surface of a human or animal body may be envisioned for use with the housing 210. It should further be appreciated that other extremities such as a hand, wrist, toe or foot may be mated by the housing 210 to the probe 212 or healthcare device.

In accordance with the embodiment as shown in FIGS. 7-9, the housing 210 is adapted to substantially surround the extremity 214. In some embodiments, the housing 210 is comprised of a flexible material, such as a latex rubber, or a fabric. The flexible material may also be adhesive so as to stick to the extremity 214. In other embodiments, the housing 210 is comprised of a substantially rigid material that may generally immobilize the extremity 214. The housing 210 comprises proximate ends 216' and 216", a distal end 218, and center portions 220' and 220". Center portion 220' connects proximate end 216' to 218. Similarly, center portion 220" connects proximate end 216" to distal end 218.

When not substantially surrounding the extremity 214 (i.e., before the housing 210 is positioned about the extremity 214 for receiving the ultrasound probe 212 to perform the imaging procedure), the housing 210 may be substantially planar, as depicted in FIG. 8. However, to substantially surround extremity 214, as depicted in FIG. 7, the housing 210 is bent at distal end 218, thereby bringing proximal ends 216' and 216" in closer proximity to one another. In this position, the proximate ends 216' and 216" form an opening 222 that is adapted to receive the extremity 214. Additionally, in this position, each of the center portions 220' and 220" includes a depression or groove 217 that together form an opening 224, similar to openings 24 and 124 (see FIGS. 2 and 5, respectively), configured to releasably receive and maintain the probe 212.

Turning now to FIG. 9, a cross-section of housing 210 at center portions 220' and 220" is depicted taken along line C-C in FIG. 7. The center portions 220' and 220" are each generally curved and, collectively, are configured so as to generally surround the extremity 214 (not shown) when positioned for releasably receiving the probe 212. The center portion 220 comprises a groove 217 that is adapted to releasably receive the ultrasound probe 212. When the ultrasound probe 212 is received by housing 210 via groove 217, the probe 212 is positioned in contact with extremity 214.

Figure 10:
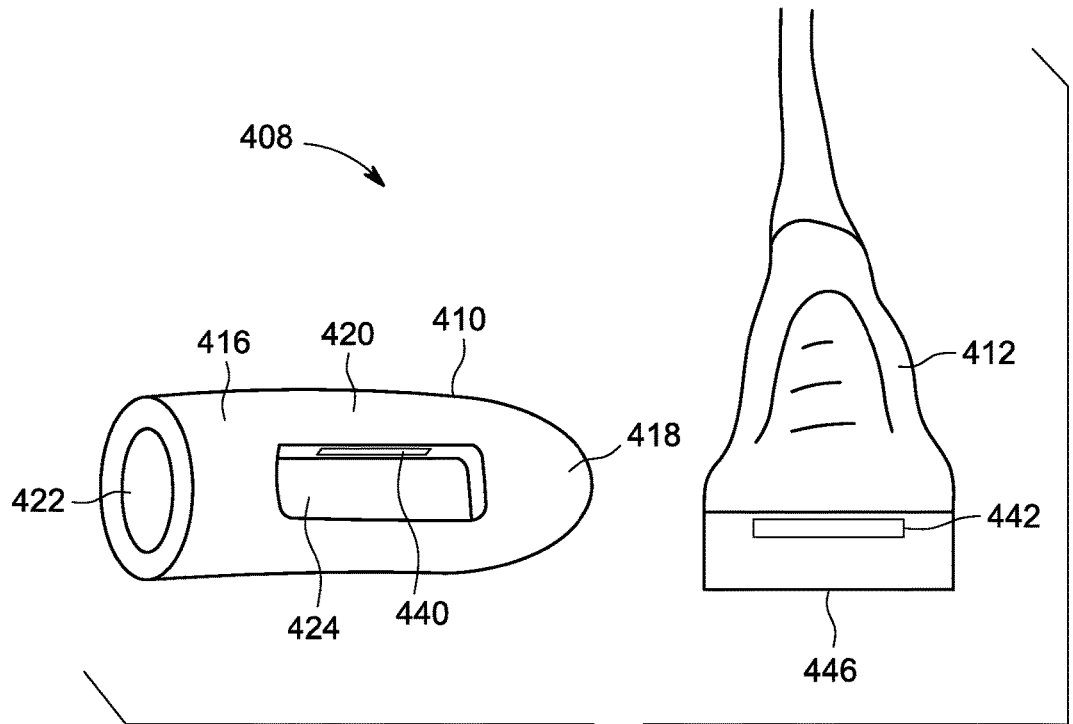
FIG. 10 is a perspective view of a system in accordance with an embodiment.

Referring to FIG. 10, a perspective view of a system 408 is shown in accordance with another embodiment. System 408 could be similar to any of the embodiments by any of systems 8, 108 and 208, except as otherwise noted below. System 408 comprises a housing 410 and a probe 412. The housing 410 comprises a proximate end 416, a distal end 418, and a center portion 420 connecting the proximate end 416 to the distal end 418. The center portion 420 comprises an opening 424 that is adapted to releasably receive the ultrasound probe 412.

The housing 410 further comprises a first mating element 440. The first mating element 440 may comprise a physical feature such as an indentation or a protrusion, or a combination thereof. It should be appreciated, however, that other embodiments of first mating element 440 may be envisioned.

The probe 412 comprises a front transducer face or tip 446 located at a distal end of the probe 412. The tip 446 is configured to come into to contact with the extremity (not shown) when fully inserted into opening 424. The probe 412 further comprises a second mating element 442. The second mating element 442 may be integral to the probe 412 or may, alternatively, be detachably coupled to the probe 412 in order to accommodate different sized probes. The second mating element 442 may comprise a physical feature such as an indentation or a protrusion, or a combination thereof. It should be appreciated, however, that other embodiments of the second mating element 442 may be envisioned.

The first mating element 440 is complementary to the second mating element 442. When the housing 410 is firmly received within the opening 424 and in close contact with the extremity 414, the first mating element 440 will be mated to the second mating element 442, and the tip 446 of the probe 412 will be positioned in proper contact with the extremity (not shown).

Further embodiments of system 8 are envisioned. For example, the system 8 may comprise a plurality of housings 10, each with opening 24 of various sizes configured to mate with a plurality of probes 12 that are of various dimensions or sizes. In another example, the system 8 may comprise a plurality of housings 10 that are of different sizes and are therefore adapted for different sized extremities. In yet another example, the probe 12 may comprise a spacer that is adapted to releasable mate with opening 24. The system 8 may comprise a plurality of spacers that are adapted to fit a plurality of probes 12, so that the plurality of probes 12 are adapted to be received by housing 10 comprising opening 24 of a single size and geometry.

Figure 11:
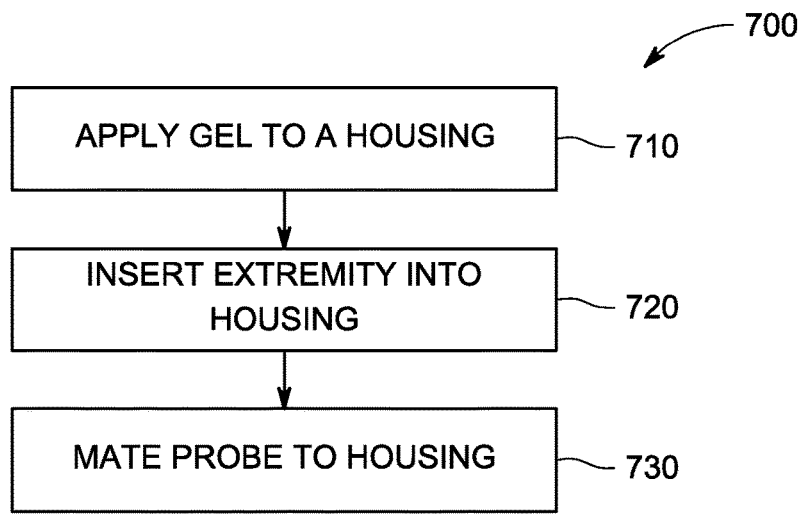
FIG. 11 is a flow diagram illustrating a method in accordance with an embodiment of the disclosure.

Having described various embodiments of the housing 10, 110, 210 and 410, an exemplary method 700 of performing an ultrasound scan on a patient extremity utilizing ultrasound probe 12, 112, 212 and 412, respectively, will now be described in connection with FIG. 11.

The method 700 may include a step 710 comprising applying ultrasonic gel to an interior of the housing 10, 110, 210 or 410. By applying gel to the interior of housing 10, 110, 210, or 410, the housing may be easily rotated about the extremity, or in some embodiments along the extremity, to obtain different images. Alternatively, the housing 10, 110, 210 or 410 could be positioned about the extremity prior to applying the gel, in which case the gel could be applied to the extremity through the opening 24, 124, 224 or 424, respectively. Alternatively, the ultrasonic gel could be applied to the extremity before the housing 10, 110, 210, 410 is positioned about the extremity. In any case, the ultrasonic gel may be any medium known in the art to conduct ultrasound waves from probe 12, 112, 212 or 412 to the imaging target, (i.e., the extremity).

The method 700 may further include a step 720 comprising positioning the housing 10, 110, 210 or 410 about the extremity. In the embodiment shown in FIG. 1, this step 720 may comprise inserting the extremity 14 into opening 22 of housing 10. In the embodiment of FIGS. 7-9, this step 720 may comprise positioning the extremity 214 on the underside 228 so the distal tip of the extremity 214 is near the distal end 218 of housing 210 and then bending or molding the housing 210 at the distal end 218 about the distal tip of the extremity 214, thereby bringing proximal ends 216' and 216" in close proximity. The step 720 may also comprise rotating the housing 10, 110, 210, or 410 about the extremity.

Depending on the embodiment of housing 10, 110, 210 or 410, the method 700 may further include securing at least one tab about the extremity to immobilize the extremity, to secure the housing 10, 110, 210 or 410 thereto, and/or to allow rotational movement of the housing 10, 110, 210, or 410 about the extremity. For example, once the extremity 114 in the embodiment of FIGS. 4-6 is positioned on the underside 128, tabs 130 may be wrapped about the extremity 114.

The method 700 may include a step 730 comprising mating ultrasound probe 12, 112, 212, 412 to the housing 10, 110, 210, 410, wherein when mated, a tip of the ultrasound probe 12, 112, 212, 412 is releasably received in the opening 24, 124, 224 and 242, respectively, and thus in proper contact with the ultrasonic gel for the imaging procedure. For example, this step 730 may comprise aligning first mating element 440 with second mating element 442. The step 730 may also comprise positioning about the distal tip of probe 212 to engage the two grooves 217 and thus contact the ultrasonic gel through the opening 224.

The system and method described herein could lead to much improved inter-operator variability in musculoskeletal ultrasound studies. Additionally, the system and method would make the contact-without-pressure problem described herein less skill-dependent and increase exam quality for less experienced operators.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

I claim:

1. A system for reducing variability in ultrasound procedures on a patient's extremity, where the extremity is a finger or a toe, the system comprising:
   a housing configured to surround at least 180 degrees of a circumference of the patient's extremity, the housing-defining both a first opening and a second opening and comprising a first mating element, where the first mating element comprises one of an indentation and a protrusion, wherein the housing further comprises a proximate end, a distal end, and a center portion connecting the proximate end to the distal end, wherein the proximate end comprises the first opening configured to receive the extremity;
   an ultrasound probe comprising a front transducer face for imaging and a second mating element, where the second mating element is complementary to the first mating element and comprises the other of the indentation and the protrusion;
   wherein the first opening is configured to receive the extremity and the second opening, in combination with the first mating element and the second mating element, is configured to releasably receive the ultrasound probe and position the front transducer face of the ultrasound probe in contact with the extremity;
   wherein, when the first mating element and the second mating element are mated, the housing retains the probe in a fixed position with respect to the housing, where the front transducer face is positioned facing towards the first opening to image the patient's extremity.

2. The system of claim 1, wherein the distal end is closed.

3. The system of claim 1, wherein the distal end comprises a third opening configured to permit the extremity to extend beyond the housing.

4. The system of claim 1, wherein the center portion comprises at least one tab configured to wrap about a portion of the extremity to secure the housing to the extremity.

5. The apparatus of claim 1, wherein the housing comprises a positioning marking, wherein the positioning marking is configured to indicate transducer placement.

6. The system of claim 1, further comprising a plurality of housings of different sizes configured for different size extremities.

7. The system of claim 1, wherein the first opening comprises a groove formed by wrapping the housing around opposite sides of the extremity about a distal tip of the extremity.

8. The system of claim 1, wherein the housing comprises a flexible material.

9. A method of performing an ultrasound scan on a patient's extremity utilizing an ultrasound probe, wherein the extremity is a finger or a toe, comprising:
   applying ultrasonic gel to an interior of a housing, the housing defining a first opening configured to receive the extremity and a second opening configured to receive an ultrasound probe, wherein the housing comprises a proximate end, a distal end, and a center portion connecting the proximate end to the distal end, wherein the proximate end comprises the first opening configured to receive the extremity;
   immobilizing the extremity by positioning the housing about at least 180 degrees of a circumference of the extremity;
   mating the ultrasound probe to the housing by positioning the ultrasound probe within the second opening wherein a first mating element on the ultrasound probe mates with a second mating element on the housing in order to position a distal tip of the ultrasound probe in contact with the extremity, wherein the first mating element comprises one of an indentation and a protrusion, wherein the second mating element is complementary to the first mating element and comprises the other of the indentation and the protrusion; and
   imaging the extremity by performing an ultrasound scan with the ultrasound probe while the extremity is immobilized by the housing.

10. The method of claim 9, wherein the positioning step further comprises:
    rotating the housing about the extremity.

11. The method of claim 9, wherein the positioning step further comprises:
    securing at least one tab about the extremity to immobilize the extremity with respect to the housing.

* * * * *